(12) United States Patent
Choi et al.

(10) Patent No.: US 7,869,960 B2
(45) Date of Patent: Jan. 11, 2011

(54) METHOD AND APPARATUS FOR DETECTING BIO-COMPLEXES USING RULE-BASED TEMPLATES

(75) Inventors: Jae Hun Choi, Daejeon (KR); Jong Min Park, Jeonju (KR); Seon Hee Park, Daejeon (KR)

(73) Assignee: Electronics and Telecommunications Research Institute, Daejon (KR)

( * ) Notice: Subject to any disclaimer, the term of this patent is extended or adjusted under 35 U.S.C. 154(b) by 1037 days.

(21) Appl. No.: 11/635,553

(22) Filed: Dec. 8, 2006

(65) Prior Publication Data

US 2007/0136001 A1 Jun. 14, 2007

(30) Foreign Application Priority Data

Dec. 8, 2005 (KR) ...................... 10-2005-0120005
Jun. 22, 2006 (KR) ...................... 10-2006-0056529

(51) Int. Cl.
*G01N 33/48* (2006.01)
(52) U.S. Cl. ....................................................... 702/19
(58) Field of Classification Search ................... 702/19
See application file for complete search history.

(56) References Cited

FOREIGN PATENT DOCUMENTS

| | | |
|---|---|---|
| JP | 2000-222421 | 8/2000 |
| KR | 10-2004-0026226 A1 | 3/2004 |
| KR | 1020040055893 | 6/2004 |
| KR | 1020050054377 | 6/2005 |
| KR | 1020060064437 | 6/2006 |

OTHER PUBLICATIONS

T. Oyama et al., Extraction of knowledge on protein-protein interaction by association rule discovery, Bioinformatics, vol. 18, No. 5, 2002, pp. 705-714.

*Primary Examiner*—Jerry Lin
(74) *Attorney, Agent, or Firm*—Lowe Hauptman Ham & Berner LLP

(57) ABSTRACT

Provided are a method and apparatus for detecting bio-complexes that are important sub protein interaction networks using a rule-based template in large interaction networks present in a single species. The method includes (a) defining a rule-based template corresponding to a bio-complex to be detected by defining a node that consists of at least one protein, a triplet that consists of two defined nodes and a protein interaction relationship therebetween, and single and composite rules using the triplet and an operator; (b) analyzing the rules of the defined rule-based template by analyzing whether the protein corresponding to the node included in the defined rule-based template and the protein interaction relationship corresponding to the triplet are present in a protein interaction network; and (c) detecting a bio-complex in the protein interaction network by assessing the triplet included in the rules analyzed and the node included in the triplet using a protein interaction relationship and protein of the protein interaction networks.

9 Claims, 7 Drawing Sheets

- ASSESS NODE
  - n1 → { p1 }
  - n2 → { p2, p4 }
  - n3 → { p3 }
  - n4 → { p3, p4 }
  - n5 → { p5 }

- ASSESS TRIPLET
  - t1=(r1,n1,n2) → { (r1,p1,p2) }, { (r1,p1,p4) }
  - t2=(r2,n2,n3) → { (r2,p2,p3) }
  - t3=(r3,n4,n5) → { (r3,p3,p5) }, { (r3,p4,p5) }

- ASSESS RULE
  - R1 → t1·t2 → {(r1,p1,p2), (r2,p2,p3)}
  - R2 → R1∗t3 → (t1·t2)∗t3 → {(r1,p1,p2), (r2,p2,p3), (r3,p3,p5)} {(r1,p1,p2), (r2,p2,p3), (r3,p4,p5)}

METHOD AND APPARATUS FOR DETECTING BIO-COMPLEXES USING RULE-BASED TEMPLATES

CROSS-REFERENCE TO RELATED PATENT APPLICATIONS

This application claims the benefit of Korean Patent Application No. 10-2005-0120005, filed on Dec. 8, 2005, and Korean Patent Application No. 10-2006-0056529, filed on Jun. 22, 2006 in the Korean Intellectual Property Office, the disclosure of which is incorporated herein in its entirety by reference.

BACKGROUND OF THE INVENTION

1. Field of the Invention

The present invention relates to a method and apparatus for detecting important sub networks in large interaction networks.

2. Description of the Related Art

In general, a single protein has a unique function, and interacts with other proteins to perform specific biological functions in a living body. Accordingly, there are complex interaction relationships between many proteins in a single cell. In addition, many proteins form a single complex to perform a unique function, such as hemoglobin or DNA replication.

Currently, Yeast Two-Hybrid that is a biological technique is used to extract protein interaction networks, and its data includes biological interaction network database (BIND), database of interacting protein (DIP) etc. In addition, a mass spectrometry can be used to identify a complex. However, these techniques are suitable for extraction of only one complex. That is, they cannot be used to detect different complexes having similar patterns present in a network.

Thus, in order to detect different complexes, the same experiment must be repeated so that the testing costs increase. In addition, these techniques can be carried out to test protein complexes alone, but cannot find out a logical protein interaction, such as a bio signal delivery pathway in protein interaction networks. The invention disclosed in the present application aims at finding such logical protein interactions.

In order to solve this problem, a sub network graph that is identical to a given network graph can be found in the entire network graph, based on a graph theory. For example, an isomorphism concordance algorithm and a sub isomorphism concordance algorithm can be used. The isomorphism concordance algorithm is used to detect a sub graph where the structure of a graph is completely identical to respective nodes, and the sub isomorphism concordance algorithm is used to detect a sub graph where the structure of a graph is completely or conceptually identical to respective nodes. However, this method cannot be used to detect various types of complexes due to limitation on expression of a graph. In addition, use of the graph theory in detecting complexes has not been made.

SUMMARY OF THE INVENTION

The present invention provides a method of automatically detecting various types of important bio-complexes in large protein interaction networks using rule-based templates at low costs.

The present invention also provides an apparatus for automatically detecting various types of important bio-complexes in large protein interaction networks using rule-based templates at low costs.

The present invention also provides a computer readable recording medium in which a program used to perform the method of detecting bio-complexes in a computer is recorded.

According to an aspect of the present invention, there is provided a method of detecting bio-complexes in protein interaction networks, the method comprising: (a) defining a rule-based template corresponding to a bio-complex to be detected by defining a node that consists of at least one protein, a triplet that consists of two defined nodes and a protein interaction relationship therebetween, and single rules and composite rules using the triplet and an operator; (b) analyzing the rules of the defined rule-based template by analyzing whether the protein corresponding to the node included in the defined rule-based template and the protein interaction relationship corresponding to the triplet are present in a protein interaction network; and (c) detecting a bio-complex in the protein interaction network by assessing the triplet included in the rules analyzed and the node included in the triplet using a protein interaction relationship and protein of the protein interaction network.

Operation (a) comprises: defining a node that is to be included in the rule-based template and that consists of at least one protein using a name, a reference, and an ontology term; defining a triplet that is included in the rule-based template and that consists of two defined nodes and a relationship therebetween that is defined using a name, direction, and degree of relationship; defining a single rule that is to be included in the rule-based template using the defined triplet or a rule which has been already defined; and defining a composite rule that is included in the rule-based template using the triplet defined, the rule which has been already defined, and an operator.

Operation (b) comprises: analyzing whether the protein corresponding to the node included in the rule-based template defined is present in the protein interaction network; analyzing whether the protein interaction relationship corresponding to the triplet included in the defined rule-based template is present in the protein interaction network; and analyzing a composite rule by converting the composite rule into a single rule such that the composite rule involves only analyzed triplets and operators.

Operation (c) comprises: changing a middle-ranking operator rule into a low-ranking operator rule in the rule-based template defined corresponding to a complex to be detected; separating items included in the low-ranking operator rule; from the separated items, assessing the triplet and two proteins included in the triplet using a protein interaction relationship and a protein of the protein interaction network; and from the separated items, assessing a basic operator and a triplet operator that can be converted from the basic operator.

According to another aspect of the present invention, there is provided an apparatus for detecting bio-complexes, the apparatus including: a template defining unit that defines a rule-based template corresponding to a bio-complex to be detected by defining a node that consists of at least one protein, defining a triplet that consists of two defined nodes and a protein interaction relationship therebetween, and defining single rules and composite rules using the triplet and an operator; a rule analyzing unit that analyzes the rules of the defined rule-based template by analyzing whether the protein of the node and the protein interaction relationship of the triplet are present in a protein interaction network; and a rule assessing unit that assesses the triplet included in the analyzed rules and the node included in the triplet using the protein interaction relationship and a protein of the protein interaction network in order to detect a bio-complex that complies with the rule in the protein interaction network.

The template defining unit is performed by defining a node that is to be included in the rule-based template and that consists of at least one protein using a name, a reference, and an ontology term; defining a triplet that is to be included in the rule-based template and that consists of two defined nodes and a protein interaction relationship therebetween, the triplet being using a name, direction, and degree of relationship; defining a single rule that is to be included in the rule-based template using the defined triplet or a rule which has been already defined; and defining a composite rule that is to be included in the rule-based template using the defined triplet, a rule which has been already defined, and an operator.

The rule analyzing unit is performed by analyzing whether the protein corresponding to the node included in the defined rule-based template is present in the protein interaction network; analyzing whether the protein interaction relationship corresponding to the triplet included in the defined rule-based template is present in the protein interaction network; and analyzing a composite rule by converting the composite rule into a single rule such that the composite rule consists of only analyzed triplets and operators.

The rule assessing unit is performed by changing a middle-ranking operator rule into a low-ranking operator rule in the defined template corresponding to a complex to be detected; separating rule items included in the low-ranking operator rule; from the separated items, assessing the triplet and two proteins included in the triplet using a protein interaction relationship and protein of the protein interaction network; and from the separated items, assessing a basic operator and a triplet operator that can be converted from the basic operator.

According to another aspect of the present invention, there is provided a computer readable recording medium in which a program used to perform the method of detecting bio-complexes in the protein interaction network in a computer is recorded.

BRIEF DESCRIPTION OF THE DRAWINGS

The above and other features and advantages of the present invention will become more apparent by describing in detail exemplary embodiments thereof with reference to the attached drawings in which.

DETAILED DESCRIPTION OF THE INVENTION

The present invention will now be described more fully with reference to the accompanying drawings.

Figure 1:
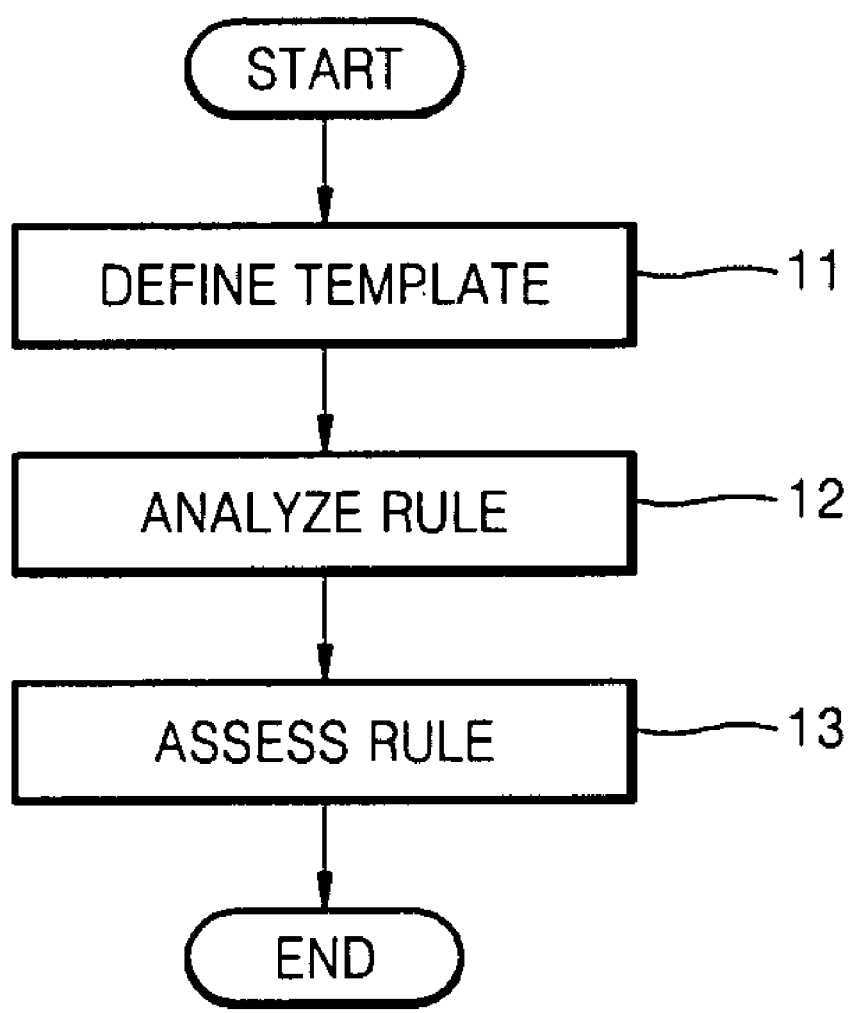
FIG. 1 is a flow chart illustrating a method of detecting bio-complexes using rule-based templates according to an embodiment of the present invention.

FIG. 1 is a flow chart illustrating a method of detecting bio-complexes using rule-based templates according to an embodiment of the present invention.

Referring to FIG. 1, in order to detect bio-complexes in a protein interaction network, a rule-based template corresponding to a complex to be detected is defined (Operation 11). In Operation 11, a node that consists of at least one protein is defined; a triplet that consists of two defined nodes and one relationship; and a single rule and a composite rule are defined using the triplet or an operator.

Then, a defined rule in the template is analyzed (Operation 12). In Operation 12, whether a protein corresponding to the node included in the defined template and the protein interaction relationship corresponding to the node are present in the protein interaction network is analyzed.

Subsequently, a bio-complex that complies with the rule is detected in the protein interaction network (Operation 13). In Operation 13, the triplet included in the rule analyzed and the nodes included in the triplet are assessed using a protein interaction relationship and a protein of the protein interaction network.

Figure 2:
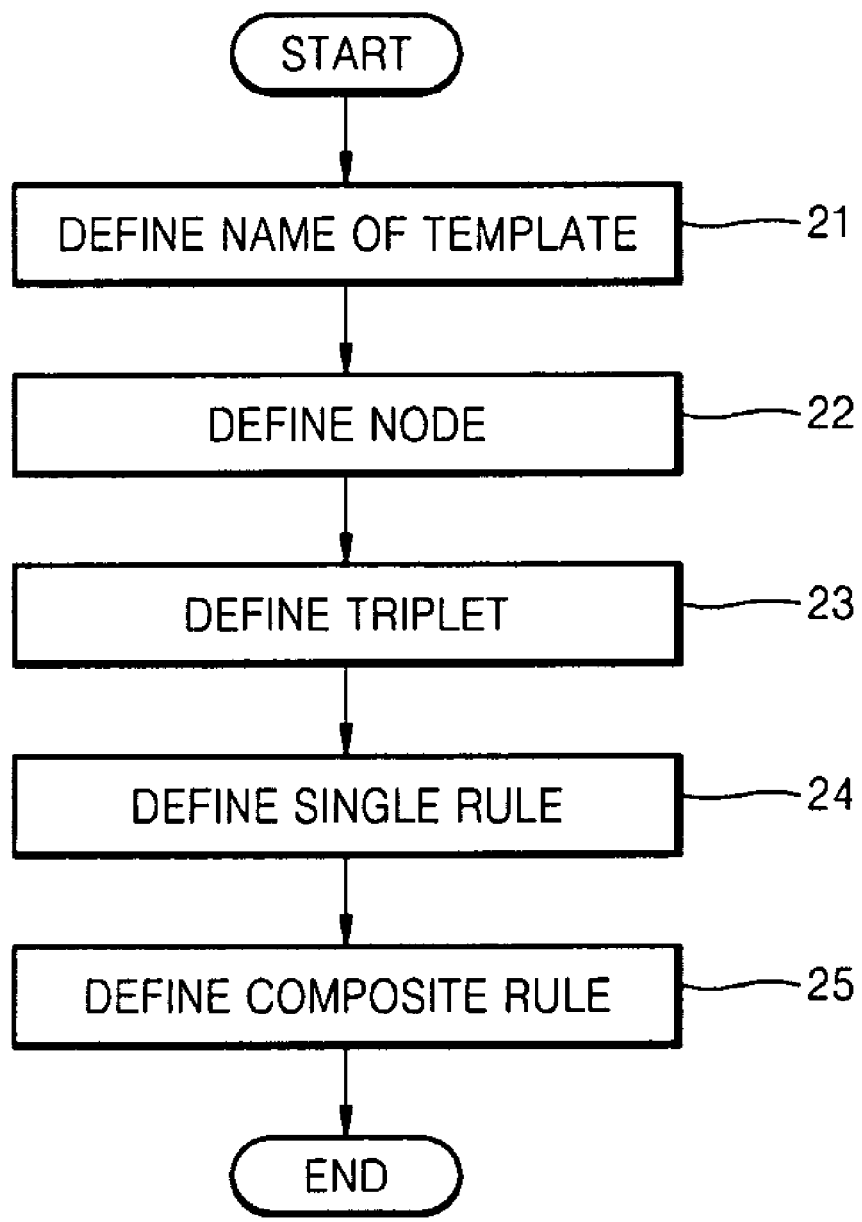
FIG. 2 is a flow chart illustrating an operation of defining a template of FIG. 1 according to an embodiment of the present invention.

FIG. 2 is a flow chart illustrating an operation of defining a template of FIG. 1 according to an embodiment of the present invention.

Referring to FIG. 2, in order to define a template, a name of the template is defined (Operation 21). Then, a node that is included in the template and consists of at least one protein is defined using a name, a reference, and an ontology term (Operation 22). When the node is defined using the ontology term, the node can be defined into various proteins.

Subsequently, a triplet that is included in the template and consists of two defined nodes and a relationship therebetween that is defined using a name, direction, and degree of relationship is defined (Operation 23). Then, a single rule included in the template is defined using the defined triplet as described above or a rule which has been already defined (Operation 24).

Subsequently, a composite rule included in the template is defined using the defined triplet as described above, the rule which has been already defined, and an operator (Operation 25). In this case, four basic operators can be used and can be changed into various forms. The four basic operators include arbitrary, association, conjunction and disjunction. The arbitrary and association are product operators, and the conjunction and disjunction are logic operators. The arbitrary operation is performed by combining two networks corresponding to respective triplets, and the association operation is performed by combining two networks in the case that in the two network sets, triplets share at least one protein. The conjunction operation is assessed using networks that consist of the same triplets in two network sets, and the disjunction operation is assessed using the union of two network sets.

Figure 3:
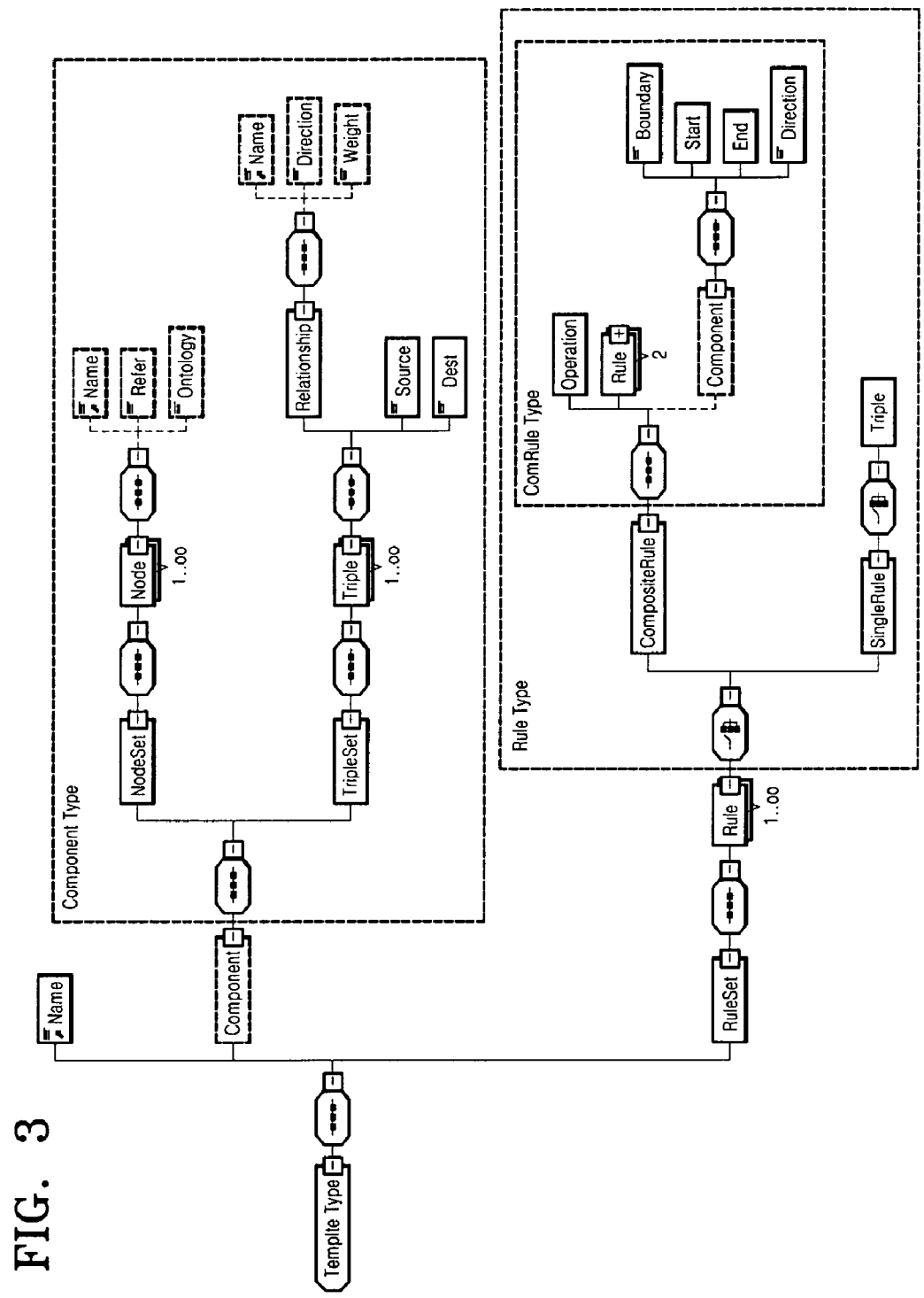
FIG. 3 illustrates a XML schema of the template of FIG. 2.

FIG. 3 illustrates a XML schema of the template of FIG. 2. Referring to FIG. 3, the template defined as described above consists of a name, a component, and a rule set; the component consists of a node set and a triplet set; and the rule set consists of a composite rule and a single rule.

Figure 4:
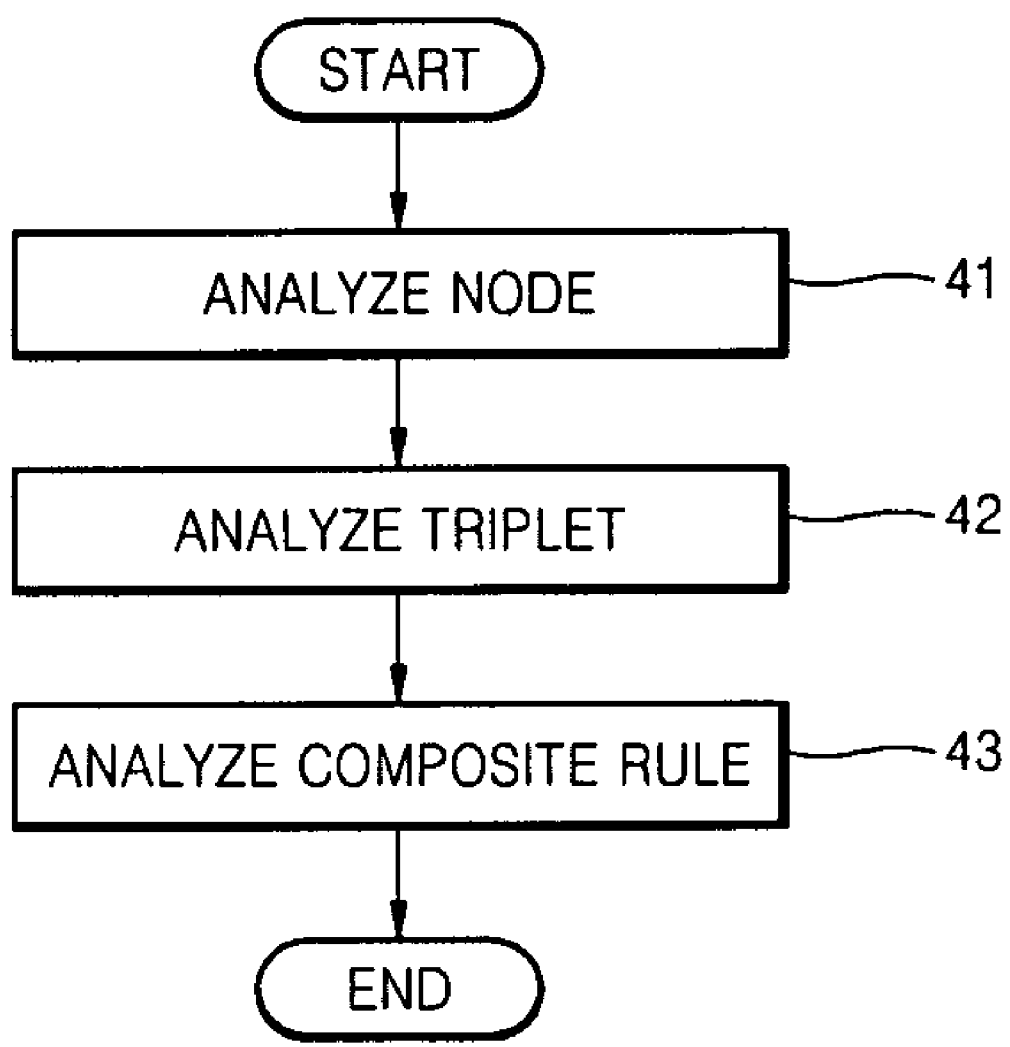
FIG. 4 is a flow chart illustrating an operation of analyzing a rule of the template of FIG. 1 according to an embodiment of the present invention.

FIG. 4 is a flow chart illustrating an operation of analyzing a rule of the template of FIG. 1 according to an embodiment of the present invention.

Referring to FIG. 4, whether the protein corresponding to the node included in the defined template is present in the protein interaction network is analyzed (Operation 41). Then, whether the protein interaction relationship corresponding to the triplet included in the defined template is present in the protein interaction network is analyzed (Operation 42). At this time, the information of protein analyzed as described above is used. Then, a composite rule included in the defined template can be analyzed by converting the composite rule into a single rule such that the composite rule consists of only triplets analyzed and operators (Operation 43).

Figure 5:
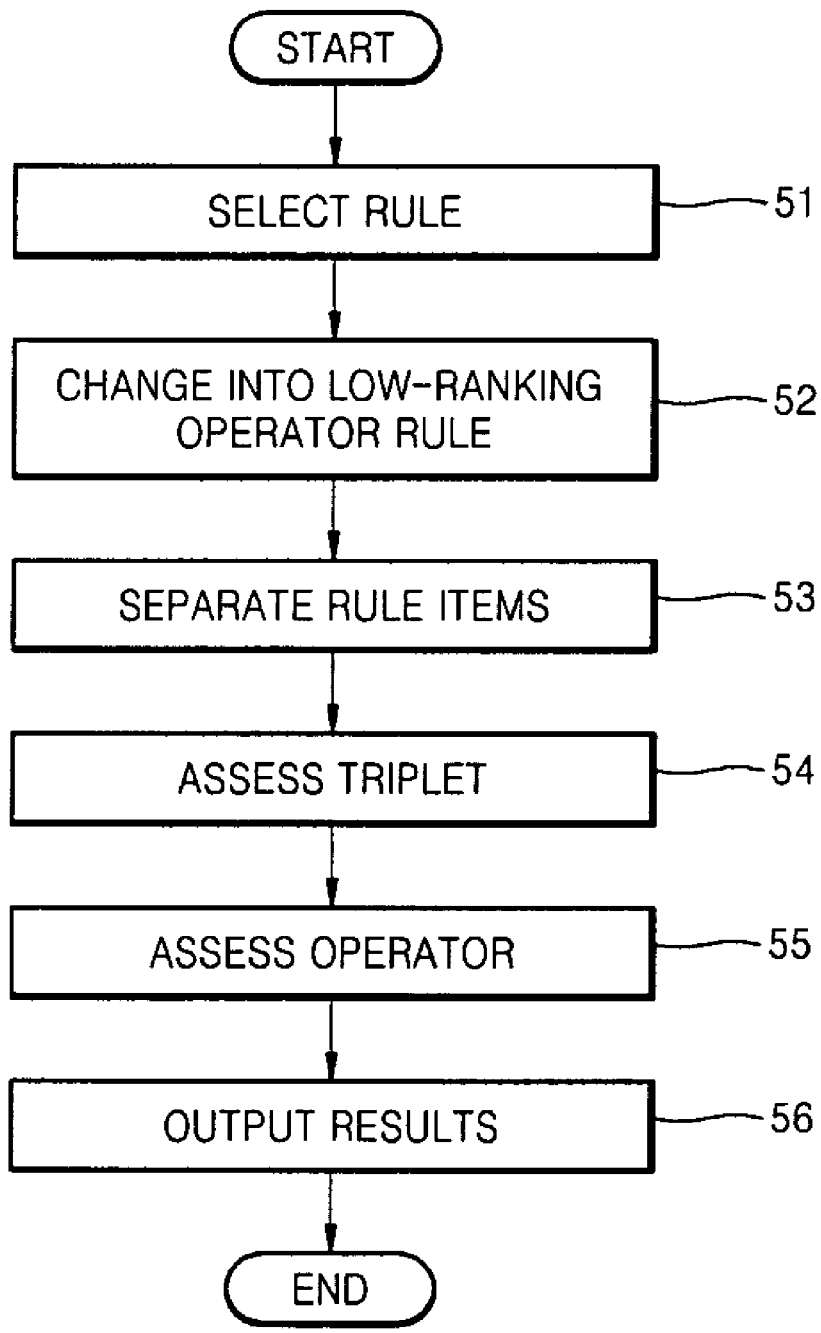
FIG. 5 is a flow chart illustrating an operation of assessing a rule of the template of FIG. 1 according to an embodiment of the present invention.

FIG. 5 is a flow chart illustrating an operation of assessing a rule of the template of FIG. 1 according to an embodiment of the present invention Referring to FIG. 5, a rule corresponding to a complex that is to be detected is selected (Operation 51), and in the defined template corresponding to the complex that is to be detected, a middle-ranking operator rule is changed into a low-ranking operator rule (Operation 52). Then, rule items included in the low-ranking operation rule are separated (Operation 53), and in the separated items, the triplet and two proteins included in the triplet are assessed using a protein interaction relationship and protein of the protein interaction network (Operation 54). A node defined using an ontology term can be assessed into various proteins or a relationship. Then, in the items described above, a basic operator and a triplet operator that is convertible from the basic operator are assessed (Operation 55). Then, the results assessed are output to be provided to a user (Operation 56).

Figure 6:
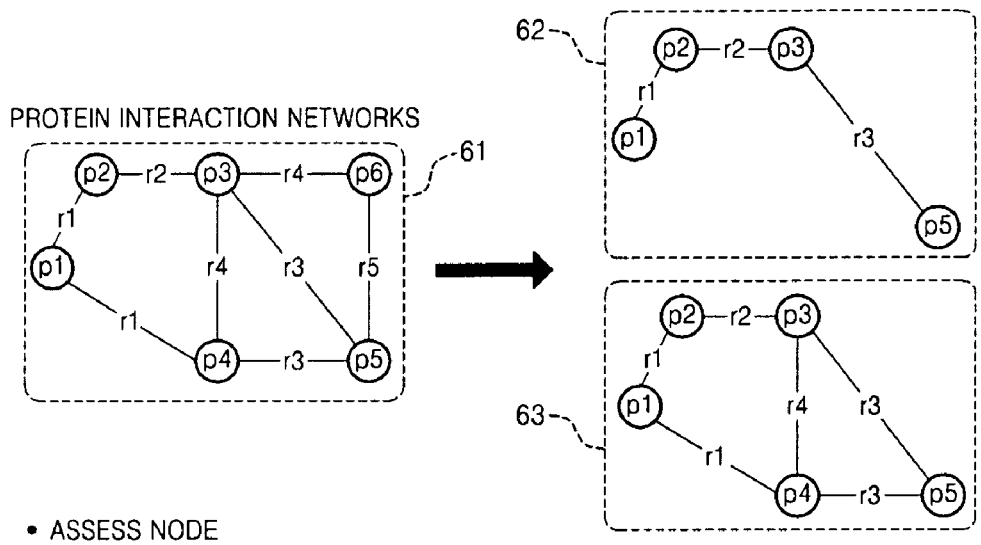
FIG. 6 illustrates an example of the operation of assessing a rule of the template of FIG. 5.

FIG. 6 illustrates an example of the operation of assessing a rule of the template of FIG. 5.

Referring to FIG. 6, two complexes 62 and 63 that comply with Rule R2 are detected in the protein interaction network 61. First, nodes and triplets are assessed. For example, Node n2 can be analyzed and assessed into Proteins p2 and p4. Accordingly, Triplet t1=(r1,n1,n2) is analyzed and assessed using a sub network having a single protein interaction relationship, such as {(r1,p1,p2)} and {(r1,p1,p4)}. Composite Rule R2→R1*t3 is converted to (t1·t2)*t3 that is an operator of R2 triplet. When this rule is assessed, two complexes that are {(r1,p1,p2), (r2,p2,p3), (r3,p3,p5)} and {(r1,p1,p2), (r2, p2,p3), (r3,p4,p5)} can be detected. The association operation '·' can be performed by combining two network sets when triplets in the two network sets share at least one protein. In [{(r1,p1,p2)},{(r1,p1,p4)})]{(r2,p2,p3)}], {(r1,p1, p2)} and {(r2,p2,p3)} share p2 so that [{(r1,p1,p2)},{(r1,p1, p4)}]-{(r2,p2,p3)}] can be assessed into {(r1,p1,p2)} and {(r2,p2,p3)}. The arbitrary operation '*' with respect to two network sets is performed by combining respectively corresponding two networks. Although [{(r1,p1,p2),(r2,p2,p3)}]* [{(r3,p4,p5)}] do not share a protein, two networks are combined to be thus assessed into a sub network, such as {(r1,p1, p2),(r2,p2,p3),(r3,p4,p5)}. The conjunction operation '∩' is assessed into networks having the same triplet in two network sets, and the disjunction operation '□' is assessed into the union of two network sets.

Figure 7:
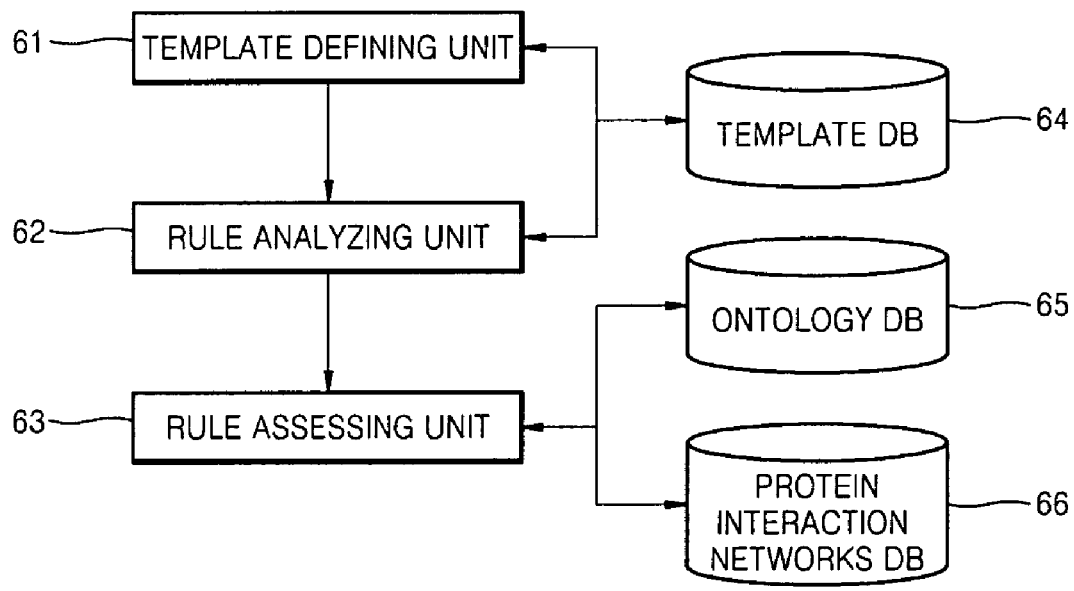
FIG. 7 is a block diagram illustrating an apparatus for detecting bio-complexes according to an embodiment of the present invention.

FIG. 7 is a block diagram illustrating an apparatus for detecting bio-complexes according to an embodiment of the present invention.

Referring to FIG. 7, the apparatus for detecting bio-complexes according to an embodiment of the present invention includes: a template defining unit 61 that defines a rule-based template corresponding to a complex to be detected by defining a node that consists of at least one protein, defining a triplet that consists of two defined nodes and one relationship, and defining single and composite rules using the triplet or an operator; a rule analyzing unit 62 that analyzes the rule defined in the template by analyzing whether the protein of the node and the protein interaction relationship of the triplet are present in the protein interaction network; and a rule analyzing unit 63 that assesses the triplet included in the analyzed rule and the node included in the triplet using the protein interaction relationship and protein of the protein interaction network in order to detect a bio-complex that complies with the rule in the protein interaction networks.

The template defining unit 61 can be performed by (a1) defining a node that is included in the template and consists of at least one protein using a name, a reference, and an ontology term; (a2) defining a triplet that is included in the template and consists of two defined nodes and a relationship therebetween that is defined using a name, direction, and degree of relationship; (a3) defining a single rule that is included in the template using the triplet defined as described above or a rule which has been already defined; and (a4) defining a composite rule that is included in the template using the triplet defined as described above, the rule which has been already defined, and an operator.

The rule analyzing unit 62 can be performed by (b1) analyzing whether the protein corresponding to the node included in the defined template is present in the protein interaction network; (b2) analyzing whether the protein interaction relationship corresponding to the triplet included in the defined template is present in protein interaction network; and (b3) analyzing a composite rule by converting the composite rule into a single rule such that the composite rule consists of only triplets analyzed and operators.

The rule assessing unit 63 can be performed by (c1) changing a middle-ranking operator rule into a low-ranking operator rule in the template corresponding to a complex to be detected; (c2) separating rule items included in the low-ranking operator rule; (c3) from separated items, assessing the triplet and two proteins included in the triplet using a protein interaction relationship and protein of the protein interaction network; and (c4) from separated items, assessing a basic operator and a triplet operator that can be converted from the basic operator.

The apparatus for detecting bio-complexes according to an embodiment of the present invention may further include a template database 64 that stores the template defined in the template defining unit 61 and provides the defined template to the rule analyzing unit 62, an ontology database 65 that provides the ontology used when a rule is assessed in the rule assessing unit 63, and a protein interaction relationship database 66 that provides a protein interaction relationship used when a rule is assessed in the rule assessing unit 63. The ontology database 65 can be a known genetic ontology database, such as SwissProt or GO. The protein interaction relationship database 66 can be database of interacting protein (DIP), biological interaction network database (BIND), or INTERACT.

The present invention can be realized as a computer readable code in a computer readable recording medium. The computer readable recording medium can be any kind of a recording apparatus in which computer readable information is stored. The computer readable recording medium can be ROM, RAM, CD-ROM, magnetic tape, floppy disc, or optical information storage, and can also be realized in the form of a carrier wave (for example, transmission through Internet). The computer readable recording medium is dispersed in a computer system connected with the network, and a code that can be read by a computer in a dispersion method is stored and executed in the computer readable recording medium.

As described above, the present invention provides a method of automatically detecting important and various forms of complexes in protein interaction networks. In this method, a template that is used to detect a complex having a specific meaning in protein interaction networks is defined using a composite rule, the composite rule of the template is changed into a single rule so that sub networks can be detected in the protein interaction network, and a complex that complies with the changed rule can be detected in the protein interaction network.

Accordingly, without expensive biological experiments, a complex having a specific meaning can be automatically detected in the protein interaction network. For example, the method and apparatus according to the present invention can be used to automatically detect a pattern similar to a signal transduction pathway of a specific disease of a mouse used as a model organism in human protein interaction networks. Accordingly, a bio-complex that causes a disease of human beings can be detected without experiments using the human beings. When the detection method according to the present invention is clinically used, bio-complexes used in high-valued medical diagnoses and the development of new drugs can be mass produced.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. A method of detecting bio-complexes in protein interaction networks, the method comprising:
    (a) defining a rule-based template corresponding to a bio-complex to be detected by defining a node that consists of at least one protein, a triplet that consists of two defined nodes and a protein interaction relationship therebetween, and single rules and composite rules using the triplet and an operator;
    (b) analyzing the rules of the defined rule-based template by analyzing whether the protein corresponding to the node included in the defined rule-based template and the protein interaction relationship corresponding to the triplet are present in a protein interaction network; and
    (c) detecting a bio-complex in a protein interaction network by assessing the triplet included in the analyzed rules and the node included in the triplet using a protein interaction relationship and protein of the protein interaction network;
    wherein the method is implemented using a computer readable code in a non-transient computer readable recording medium.

2. The method of claim 1, wherein operation (a) comprises:
    defining a node that is to be included in the rule-based template and that consists of at least one protein using a name, a reference, and an ontology term;
    defining a triplet that is to be included in the rule-based template and that consists of two defined nodes and a relationship therebetween that is defined using a name, direction, and degree of relationship;
    defining a single rule that is to be included in the rule-based template using the defined triplet or a rule which has already been defined; and
    defining a composite rule that is to be included in the rule-based template using the triplet defined, a rule which has been already defined, and an operator.

3. The method of claim 1, wherein operation (b) comprises:
    analyzing whether the protein corresponding to the node included in the rule-based template defined is present in the protein interaction network;
    analyzing whether the protein interaction relationship corresponding to the triplet included in the defined rule-based template is present in the protein interaction network; and
    analyzing a composite rule by converting the composite rule into a single rule such that the composite rule involves only analyzed triplets and operators.

4. The method of claim 1, wherein operation (c) comprises:
    changing a middle-ranking operator rule into a low-ranking operator rule in the rule-based template defined corresponding to a complex to be detected;
    separating items included in the low-ranking operator rule;
    from the separated items, assessing the triplet and two proteins included in the triplet using a protein interaction relationship and a protein of the protein interaction network; and
    from the separated items, assessing a basic operator and a triplet operator that can be converted from the basic operator.

5. A computer-controlled apparatus for detecting bio-complexes comprising:
    a template defining unit that defines a rule-based template corresponding to a bio-complex to be detected by defining a node that consists of at least one protein, defining a triplet that consists of two defined nodes and a protein interaction relationship therebetween, and defining single rules and composite rules using the triplet and an operator;
    a rule analyzing unit that analyzes the rules of the defined rule-based template by analyzing whether the protein of the node and the protein interaction relationship of the triplet are present in a protein interaction network; and
    a rule assessing unit that assesses the triplet included in the analyzed rules and the node included in the triplet using the protein interaction relationship and a protein of the protein interaction network in order to detect a bio-complex that complies with the rule in the protein interaction network.

6. The apparatus of claim 5, wherein the template defining unit performs:
    defining a node that is to be included in the rule-based template and that consists of at least one protein using a name, a reference, and an ontology term;
    defining a triplet that is to be included in the rule-based template and that consists of two defined nodes and a protein interaction relationship therebetween, the triplet being defined using a name, direction, and degree of relationship;
    defining a single rule that is to be included in the rule-based template using the defined triplet or a rule which has already been defined; and
    defining a composite rule that is to be included in the rule-based template using the defined triplet, a rule which has already been defined, and an operator.

7. The apparatus of claim 5, wherein the rule analyzing unit performs:
    analyzing whether the protein corresponding to the node included in the defined rule-based template is present in the protein interaction network;
    analyzing whether the protein interaction relationship corresponding to the triplet included in the defined rule-based template is present in the protein interaction network; and
    analyzing a composite rule by converting the composite rule into a single rule such that the composite rule consists of only analyzed triplets and operators.

8. The apparatus of claim 5, wherein the rule assessing unit performs:
    changing a middle-ranking operator rule into a low-ranking operator rule in the template defined corresponding to a complex to be detected;

separating rule items included in the low-ranking operator rule;

from the separated items, assessing the triplet and two proteins included in the triplet using a protein interaction relationship and protein of the protein interaction network; and from the separated items, assessing a basic operator and a triplet operator that can be converted from the basic operator.

9. A non-transient computer-readable recording medium with an executable program stored thereon, wherein the program instructs a microprocessor to perform instructions comprising:

(a) defining a rule-based template corresponding to a bio-complex to be detected by defining a node that consists of at least one protein, a triplet that consists of two defined nodes and a protein interaction relationship therebetween, and single rules and composite rules using the triplet and an operator;

(b) analyzing the rules of the defined rule-based template by analyzing whether the protein corresponding to the node included in the defined rule-based template and the protein interaction relationship corresponding to the triplet are present in a protein interaction network; and (c) detecting a bio-complex in a protein interaction network by assessing the triplet included in the analyzed rules and the node included in the triplet using a protein interaction relationship and protein of the protein interaction network.

* * * * *